US011590358B2

(12) United States Patent
Osypka et al.

(10) Patent No.: US 11,590,358 B2
(45) Date of Patent: Feb. 28, 2023

(54) SYSTEM AND METHOD OF USING ENDOBRONCHIAL ULTRAVIOLET LIGHT THERAPY TO TREAT PATIENTS INFECTED WITH COVID-19 CORONAVIRUS, SARS, COV-2

(71) Applicant: Oscor Inc., Palm Harbor, FL (US)

(72) Inventors: Thomas P. Osypka, Palm Harbor, FL (US); Timothy Searfoss, New Port Richey, FL (US); N R Chandrasekar, Canton, MA (US)

(73) Assignee: Osypka Technologies LLC, Safety Harbor, FL (US)

( * ) Notice: Subject to any disclaimer, the term of this patent is extended or adjusted under 35 U.S.C. 154(b) by 69 days.

(21) Appl. No.: 17/109,560

(22) Filed: Dec. 2, 2020

(65) Prior Publication Data

US 2021/0299467 A1 Sep. 30, 2021

Related U.S. Application Data

(60) Provisional application No. 63/000,217, filed on Mar. 26, 2020.

(51) Int. Cl.
*A61N 5/06* (2006.01)
(52) U.S. Cl.
CPC ......... *A61N 5/0624* (2013.01); *A61N 5/0603* (2013.01); *A61N 2005/0604* (2013.01);
(Continued)
(58) Field of Classification Search
CPC ............... A61N 5/0624; A61N 5/0603; A61N 2005/0604; A61N 2005/0632;
(Continued)

(56) References Cited

U.S. PATENT DOCUMENTS

| 7,159,590 B2 | 1/2007 | Rife |
| 8,109,981 B2 | 2/2012 | Gertner et al. |

(Continued)

FOREIGN PATENT DOCUMENTS

| CA | 3108250 A1 | 3/2020 |
| WO | 9505214 A1 | 2/1995 |

(Continued)

OTHER PUBLICATIONS

DeRudder, JL. Commercial applications of polycarbonates. Handbook of Polycarbonate Science and Technology. 2000 (Year: 2000).*

(Continued)

*Primary Examiner* — Mallika D Fairchild
*Assistant Examiner* — Shreya Anjaria
(74) *Attorney, Agent, or Firm* — Locke Lord LLP; Scott D. Wofsy

(57) ABSTRACT

A catheter is disclosed for performing ultraviolet light therapy in a pulmonary system of a patient, which includes a catheter body having opposed proximal and distal end portions, a handle assembly operatively associated with the proximal end portion of the catheter body, an illumination assembly operatively associated with the distal end portion of the catheter body and including an LED light source for generating UVC radiation, wherein the illumination assembly includes a coupler connecting the LED light source with the distal end portion of the catheter body, and an elongated braided sleeve disposed within the catheter body, wherein the coupler is adapted to transfer heat from the illumination assembly to the braided sleeve, such that the braided sleeve serves as a heat sink for the illumination assembly.

18 Claims, 11 Drawing Sheets

(52) U.S. Cl.
CPC ............ *A61N 2005/0632* (2013.01); *A61N 2005/0643* (2013.01); *A61N 2005/0651* (2013.01); *A61N 2005/0661* (2013.01)

(58) Field of Classification Search
CPC .... A61N 2005/0643; A61N 2005/0651; A61N 2005/0661; A61N 2005/005
See application file for complete search history.

(56) References Cited

U.S. PATENT DOCUMENTS

| | | | |
|---|---|---|---|
| 9,592,374 B2* | 3/2017 | Muse | A61M 39/16 |
| 10,682,203 B2 | 6/2020 | Vazales | |
| 2004/0199052 A1 | 10/2004 | Banik et al. | |
| 2006/0130846 A1 | 6/2006 | Rife | |
| 2012/0022314 A1* | 1/2012 | Sing | A61N 5/1027 600/3 |
| 2013/0204167 A1 | 8/2013 | Sverdlik et al. | |
| 2013/0211292 A1* | 8/2013 | Sverdlik | A61B 8/445 601/2 |
| 2016/0354016 A1* | 12/2016 | Benaron | A61B 5/14546 |
| 2017/0035277 A1* | 2/2017 | Kucharski | A61B 1/018 |
| 2019/0083682 A1* | 3/2019 | Littleton | A61L 29/042 |
| 2019/0175938 A1 | 6/2019 | Rezaie et al. | |
| 2019/0336714 A1* | 11/2019 | Vazales | A61M 16/0484 |
| 2019/0374751 A1* | 12/2019 | Finson | A61M 25/0662 |

FOREIGN PATENT DOCUMENTS

| | | |
|---|---|---|
| WO | 2017070155 A1 | 4/2017 |
| WO | WO-2017070155 A1 * | 4/2017 |

OTHER PUBLICATIONS

Extended European Search Report dated Aug. 17, 2021, issued during the prosecution of European Patent Applciation No. EP 21161051.4.

* cited by examiner

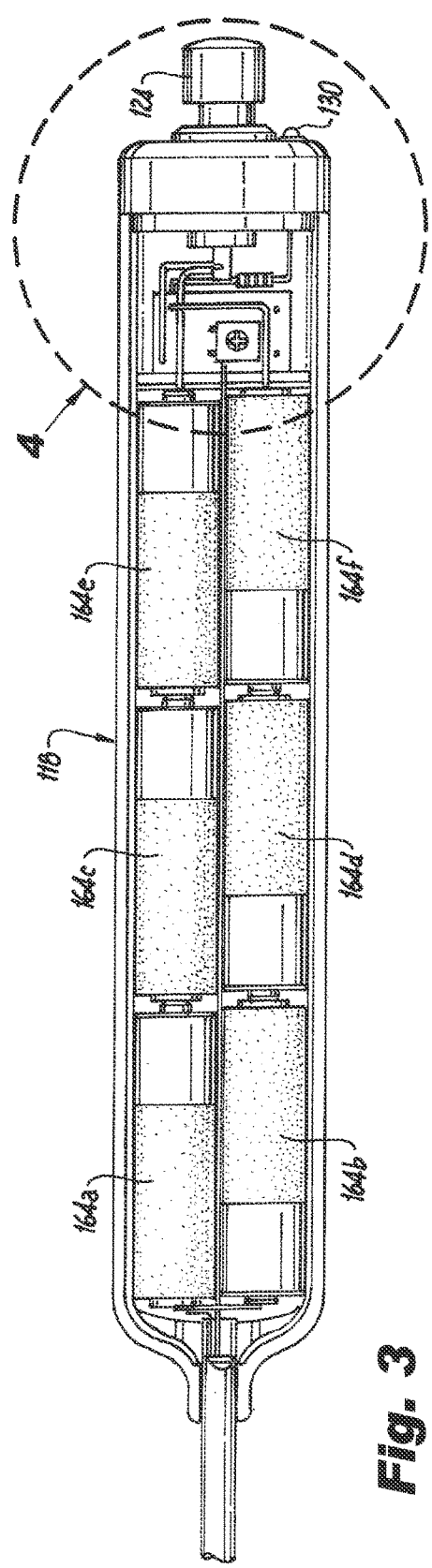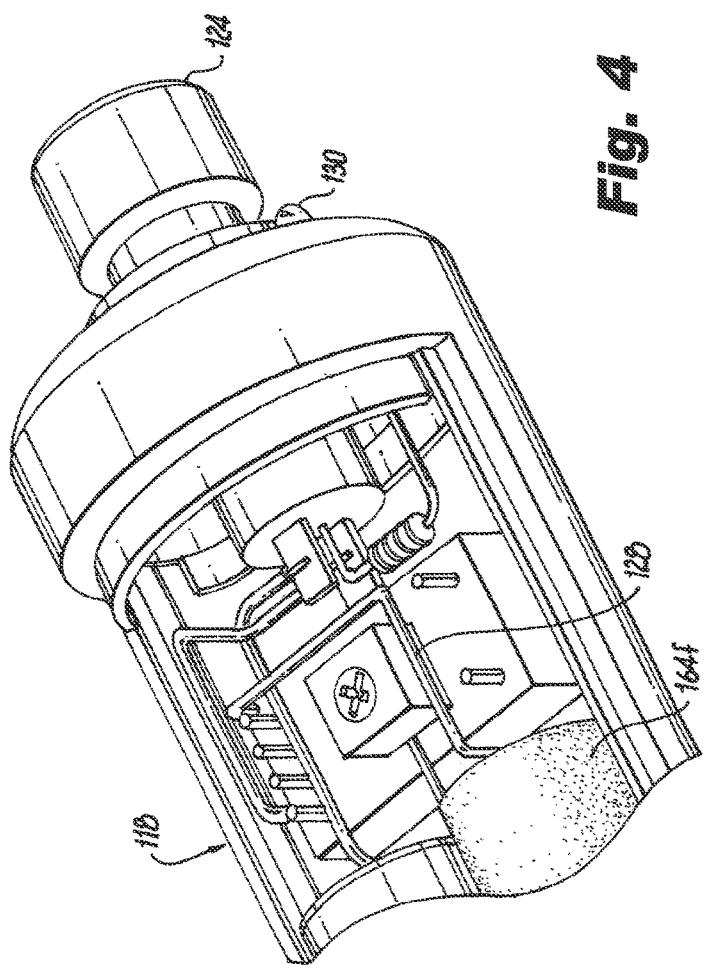
Fig. 3
Fig. 4

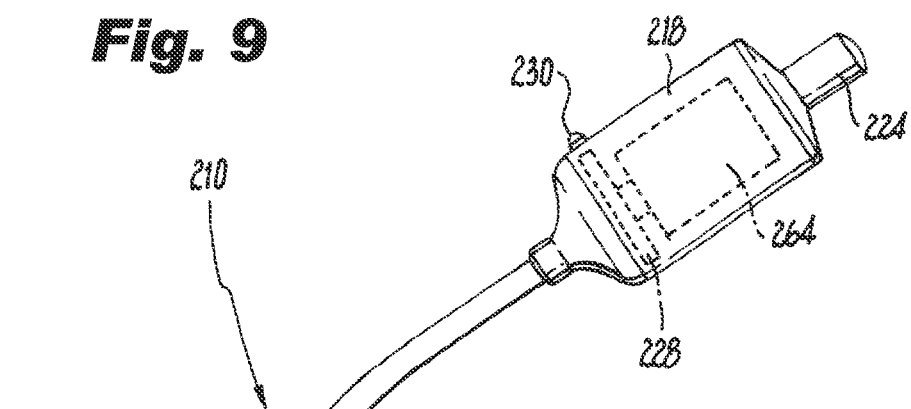
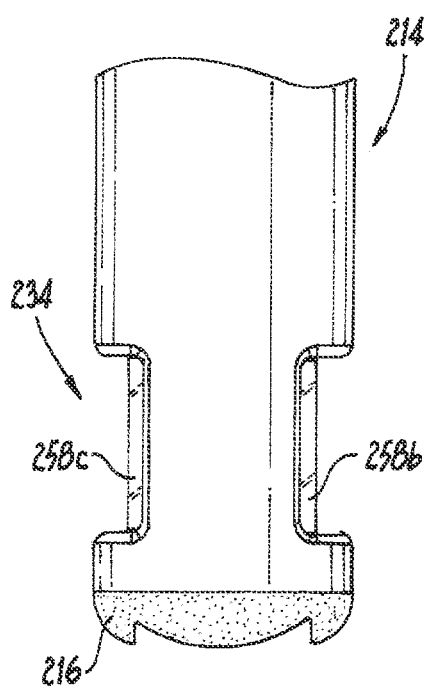
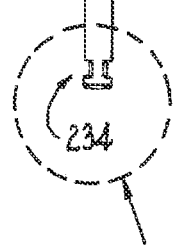
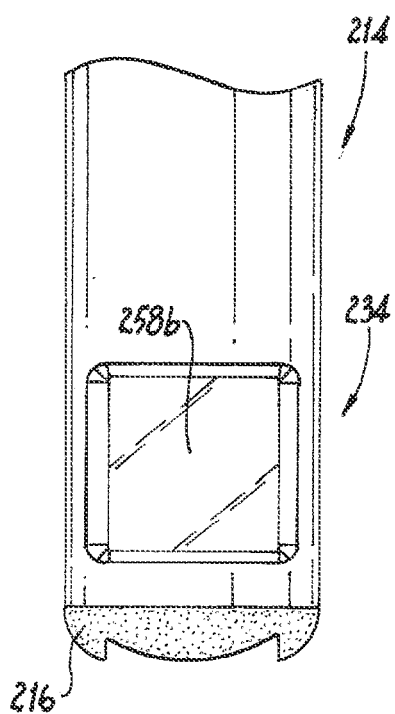
Fig. 9
Fig. 10
Fig. 11

SYSTEM AND METHOD OF USING ENDOBRONCHIAL ULTRAVIOLET LIGHT THERAPY TO TREAT PATIENTS INFECTED WITH COVID-19 CORONAVIRUS, SARS, COV-2

CROSS REFERENCE TO RELATED APPLICATION

This application claims the benefit of priority to U.S. Provisional Patent Application Ser. No. 63/000,217, filed on Mar. 26, 2020, the disclosure of which is incorporated herein by reference in its entirety.

BACKGROUND OF THE INVENTION

1. Field of the Invention

The subject invention is directed to a medical device, and more particularly, to a pulmonary endobronchial catheter system configured to emit ultraviolet light to reduce bacterial, fungal and/or viral load in patients with COVID-19 and other respiratory disease.

2. Description of Related Art

COVID-19 (coronavirus disease 2019) is a respiratory tract infection caused by a novel coronavirus, SARS-CoV-2 (initially called 2019-nCoV). As of Mar. 11, 2020, the extent of infection was declared pandemic by the World Health Organization. The virus is thought to be zoonotic in origin, but the animal reservoir is not yet known, and it is clear that human-to-human transmission is occurring. Infection ranges from asymptomatic to severe. Symptoms include fever, cough, and (in moderate to severe cases) dyspnea. The disease may evolve over the course of a week or more from mild to severe.

A significant proportion of clinically evident cases are severe. There is currently no vaccine available to prevent this infection. Thus, infection control measures are the mainstay of prevention. The mortality rate among diagnosed cases (case fatality rate) is about 2% to 3%, but true overall mortality rate is uncertain, as the total number of cases (including undiagnosed persons with milder illness) is unknown.

The viral load of severe acute respiratory syndrome coronavirus 2 (SARS-CoV-2) peaks within the first week of disease onset. To date, no specific treatment has been proven to be effective for SARS-CoV-2 or COVID 19 infection. Patients have a peak viral load about 3 days after onset of symptoms with a higher load in the nose than the throat and respiratory system. In the SARS patients, viral load peak occurred 10 days after symptom onset. Those patients also had higher viral loads later in the course of the disease in lower respiratory samples.

In the case of the Middle East Respiratory Syndrome Coronavirus (MERS-CoV), viral load peaked about the second day of hospitalization in the upper respiratory samples and about the sixth day in the lower respiratory samples. These findings parallel the findings from SARS-CoV. In addition, the peak upper respiratory tract RNA occurred on day 7-10 after onset in community cases. There is persistent viral load beyond 3 weeks in severe cases of MERS and SARS.

The total number of cases is rapidly sky rocketing globally with increased mortality rate, as there is no other definitive treatment available to reduce the viral load. Scientific literature supports reducing the viral load improves patient outcomes and reduces the mortality and morbidity, eventually reducing the burden on healthcare systems and the world economy.

As the pharmacological agents such antiviral drugs have failed to combat the disease, there is a need for an alternative approach to reducing the viral load of the patients who have tested positive and are symptomatic regardless of the respiratory failure, requiring ventilator support therapy or presenting with symptoms.

SUMMARY OF THE DISCLOSURE

The subject invention is directed to a new and useful non-pharmacologic modality using an in vivo catheter system with LED light sources embedded on microchips for emitting ultraviolet (UV) light radiance (i.e., endobronchial ultraviolet light therapy) to reduce bacterial, fungal and viral loads in patients presenting with COVID-19 Coronavirus, SARS-COV-2 and other respiratory diseases. The system can be safely used in patients on ventilator support and patients that are not on a ventilator support. Also, the nasal orifice can be treated with this device to reduce the viral load therein, to prevent distal migration of the virus to the lower respiratory system and most importantly, to prevent spreading of the disease to others from nasal secretions and from expiration of inhaled air.

The scientific literature dating from the 1960's has been documenting and demonstrating the efficacy of Ultraviolet light to reduce, or otherwise eliminate, nosocomial infections and to reduce pathogens in the operating rooms, patient rooms, and chronic care facilities caused by various microorganisms of both bacterial, viral and fungal in origin. Reduction in viral load in various samples such as blood, serum, body fluid, public water supplies and inanimate objects, has also been documented and demonstrated. But to date, the use of UV light has not been demonstrated in vivo other than treating open wounds especially in burn victims.

Studies have documented reduction of bacterial colonies in open wounds and burn victims using UV light treatment. Based on this, and taking advantage of the ultraviolet spectrum ranging from 240-350 nm which has no harmful side effects from minimal exposure for short duration, we have designed and developed a device incorporating one to several ultraviolet generating micro computer chips, which is incorporated in a device specifically designed for use within any human anatomic system, inclusive of respiratory, circulatory, genitourinary, gastrointestinal or any cavity of body cavity or lumen.

The device comprises an elongated body of an appropriate length and dimension suitable for performing such a procedure. The device comprises an external power source with a control switch to turn on and off the microchips to emit specific wavelength of ultraviolet light. The device is specifically designed to reduce the viral load in the respiratory system of patients infected with novel COVID-19 coronavirus.

A physician trained in performing routine bronchoscopy or intensive care physicians and nurses who perform routine suctioning of the bronchial system should be able to use such a device with minimal instructions. In use, the operator will turn the on/off switch to activate the ultraviolet light once introduced into the oropharyngeal or upper respiratory tract via endotracheal or bronchoscope side port. The UV light will have to remain on and the catheter can be visualized on the computer screen when used with bronchoscope.

It can also be used without the scope passed through either the right mainstem bronchus or left main stem bronchus. The switch is turned off once the apparatus is at the oral cavity level when it is withdrawn after treatment. It is highly plausible that this procedure will substantially reduce the viral load by its virucidal properties. It is not only virucidal, but it may also combat secondary bacterial pathogens causing pneumonia, which adds morbidity and mortality to these patients.

The catheter portion of the device may coated with a thermoplastic polyurethane to enhance the surface area of the luminance emitted by LEDs embedded on the microchips. This not only reduces the viral load within the bronchus but may substantial reduce the viral load in deoxygenated and oxygenated blood travelling in capillaries, arteries and veins adjacent to the bronchial tree.

In particular, the subject invention is directed to a catheter system for ultraviolet light therapy in a pulmonary system of a patient, which includes an elongated flexible tubular catheter body defining a longitudinal axis with opposed proximal and distal end portions, and having an elongated braided sleeve extending along a length thereof to provide a heat sink, a handle portion operatively associated with the proximal end portion of the elongated tubular catheter body, and an illumination assembly operatively associated with the distal end portion of the elongated tubular for emitting ultraviolet light radiance to reduce viral, fungal and/or bacterial loads in the pulmonary system of the patient and possibly total viral load in the bloodstream.

The elongated flexible tubular catheter body houses the illumination assembly, which includes a coupler that is connected to a distal end portion of the elongated tubular catheter body. The illumination assembly further includes at least one LED light source operatively connected to the coupler. The coupler is adapted and configured to transfer heat from the illumination assembly to the elongated braided sleeve, which is made up of tinned copper. The elongated braided sleeve is enclosed by a compression ring at the distal end portion of the elongated tubular catheter body. The illumination assembly is enclosed within a polycarbonate or ceramic tip cover which extends proximally therefrom for reducing surface heat.

To operate, the handle portion is adapted and configured to receive a power source for delivering power to the illumination assembly through the elongated flexible tubular catheter body. The handle portion also includes a switch for manually activating the power source in addition to an indicator for communicating to a user that the power source is activated, and can include a locking pull pin for immobilizing the switch.

The elongated tubular catheter body has an operative length of about between 40.0 to 50.0 cm and an outer diameter of about 5.5 mm, wherein conductors extend from the handle portion to the illumination assembly to deliver power from the power source. The elongated flexible tubular catheter body also includes a coating of thermoplastic polyurethane, and at the distal end of elongated flexible tubular catheter body, has an atraumatic distal tip.

The elongated flexible tubular catheter body, and in particular, the illumination assembly, houses within the atraumatic distal tip at least one LED light source which is adapted and configured to generate UVC radiation at a wavelength of about between 240-350 nm, and preferably about 265 nm. The at least one LED light source may include a first LED light source facing in a distal direction. The at least one LED light source may also include the at least one LED light source in addition to a second and third LED light sources positioned orthogonally to the first LED light source and facing in opposite lateral directions relative to the longitudinal axis of the elongated tubular catheter body. Each LED light source of the illumination assembly is supported on a microchip wherein the microchip is disposed with a housing having a quartz glass window adjacent the at least one LED light source.

Another embodiment of the subject invention is directed to a catheter for performing ultraviolet light therapy in a pulmonary system of a patient which includes an elongated flexible tubular catheter body defining a longitudinal axis with opposed proximal and distal end portions, and having an elongated braided sleeve extending along a length thereof to provide a heat sink, an illumination assembly operatively associated with the distal end portion of the elongated tubular for emitting ultraviolet light radiance to reduce viral, fungal and/or bacterial loads in the pulmonary system of the patient, wherein the illumination assembly includes an LED light source facing in a distal direction, and a handle portion operatively associated with the proximal end portion of the elongated tubular catheter body, which is adapted and configured to receive a power source for delivering power to the illumination assembly through the elongated tubular catheter body.

In this embodiment, the handle portion also includes a switch for manually activating the power source and an indicator for communicating to a user that the power source is activated. The illumination assembly of the elongated flexible tubular catheter body includes a coupler connected to a distal end portion of the elongated tubular catheter body, which is adapted and configured to transfer heat from the illumination assembly to the braided sleeve. Within the illumination assembly, the LED light source is adapted and configured to generate UVC radiation at a wavelength of about between 240-350 nm, and preferably about 265 nm. The LED light source is supported on a microchip, wherein the microchip is disposed with a housing having a quartz glass window adjacent the LED light source.

In a preferred embodiment of the subject invention, the catheter includes an elongated flexible catheter body defining a longitudinal axis and having opposed proximal and distal end portions, a handle assembly operatively associated with the proximal end portion of the catheter body, an illumination assembly operatively associated with the distal end portion of the catheter body and including an LED light source facing in a distal direction for generating UVC radiation at a wavelength of about 265 nm, wherein the illumination assembly includes a coupler connecting the LED light source with the distal end portion of the catheter body, and an elongated braided sleeve formed from tinned copper and disposed within the catheter body along a length thereof, wherein the coupler is adapted to transfer heat from the illumination assembly to the braided sleeve, such that the braided sleeve serves as a heat sink for the illumination assembly.

During treatment with either embodiment, the source of UVC radiation is introduced into the endobronchial pulmonary system of a patient through an endobronchial tube or directly via the side port of a bronchoscope by way of an elongated tubular catheter tip into the lumen of bronchi of the pulmonary system or through a ventilator tube by way of an elongated catheter. Alternatively, the source of UVC radiation can be introduced into the pulmonary system of a patient through an endotracheal tube or through a bronchoscope. The device can be manually rotated by a user to provide ultraviolet therapy circumferentially and axially.

In summary, hereby provided is a novel non-pharmacological, nontoxic agent to combat COVID-19 coronavirus, since at the present time there is no vaccine or any pharmacological agent. The device can be used with minimal training by healthcare personnel to reduce the viral load in patients presenting with COVID-19 and other acute respiratory symptoms. By reducing the viral load, rates of mortality and morbidity can be potentially reduced. With this novel device and procedure, several patients can be treated as outpatients and avoid admission to the hospital.

BRIEF DESCRIPTION OF THE DRAWINGS

So that those skilled in the art will readily understand how to make and use the pulmonary endobronchial (EB) catheter system of the subject invention without undue experimentation, preferred embodiments thereof will be described in detail herein below with reference to the figures wherein:

FIG. 3 is a cross-sectional view of the handle portion of the catheter device shown in FIG. 1;

FIG. 4 is enlarged localized perspective view of the internal circuitry of the handle portion of FIG. 1 showing circuitry contained therein;

FIG. 9 is a perspective view of another embodiment of the catheter device of the subject invention, which has three LED light sources at the distal end thereof;

FIGS. 10 and 11 are enlarged elevational views of the illumination assembly of the catheter device shown in FIG. 9;

DETAILED DESCRIPTION OF THE PREFERRED EMBODIMENTS

Figure 1:
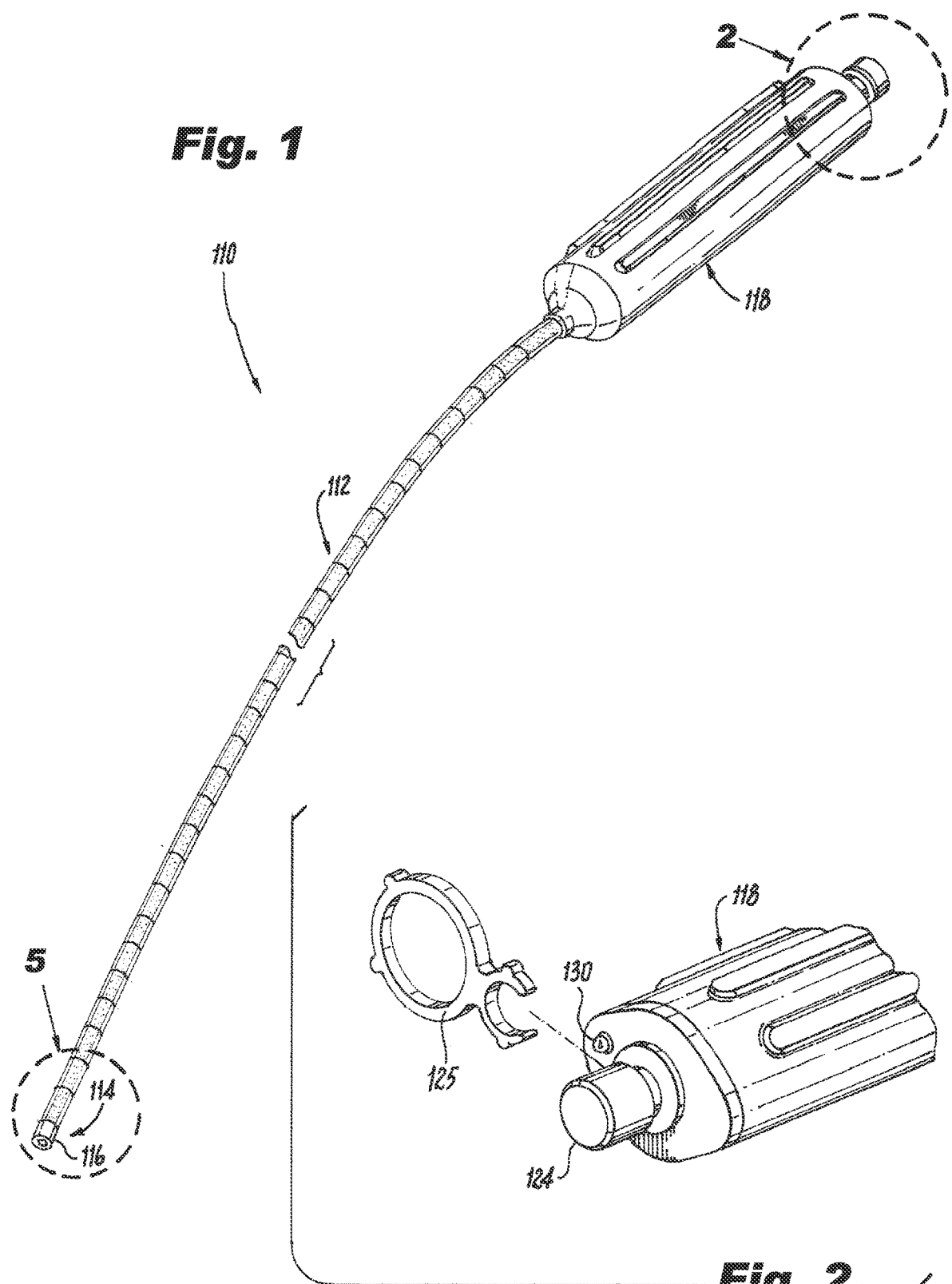
FIG. 1 is a perspective view of the catheter device of the subject invention with one LED light source at a distal end thereof.

Referring now to the drawings wherein like reference numerals identify similar structural elements and features of the subject invention, there is illustrated in FIG. 1 a catheter device constructed in accordance with a preferred embodiment of the subject invention and designated generally by reference number 110. Catheter device 110 is adapted and configured for performing ultraviolet light therapy in a pulmonary system of a patient, using one or more LED light sources, to reduce viral, fungal and/or bacterial loads. The catheter device is a sterile, single use device that can be readily discarded after use.

The catheter device 110 includes an elongated flexible tubular catheter body 112 having an outer diameter of about 5.50 mm and an operative length of about between 40 to 50 cm or greater. Preferably, markings or indicia are provided along the length of the catheter body 112 in 5.0 cm increments for visualization during a procedure. The distal end portion 114 of the elongated flexible catheter body 112 has an atraumatic cylindrical tip section 116 that encases and protects the LED light source(s), as described in more detail below.

Catheter device 110 further includes a proximal handle assembly 118 that is operatively associated with a proximal end portion of the catheter body 112. The handle assembly 118 has raised features for enhanced gripping. The handle assembly 118 defines an interior cavity that houses a plurality of batteries or power cells 164a-164f for powering the catheter device 110, as shown in FIG. 3, and a controller 128 with suitable electronics and circuitry for controlling the operation and functions of the catheter device 110, as shown in FIG. 4. It is envisioned that the catheter device 110 may be powered by an external power source instead of batteries 164a-164f.

Figure 2:
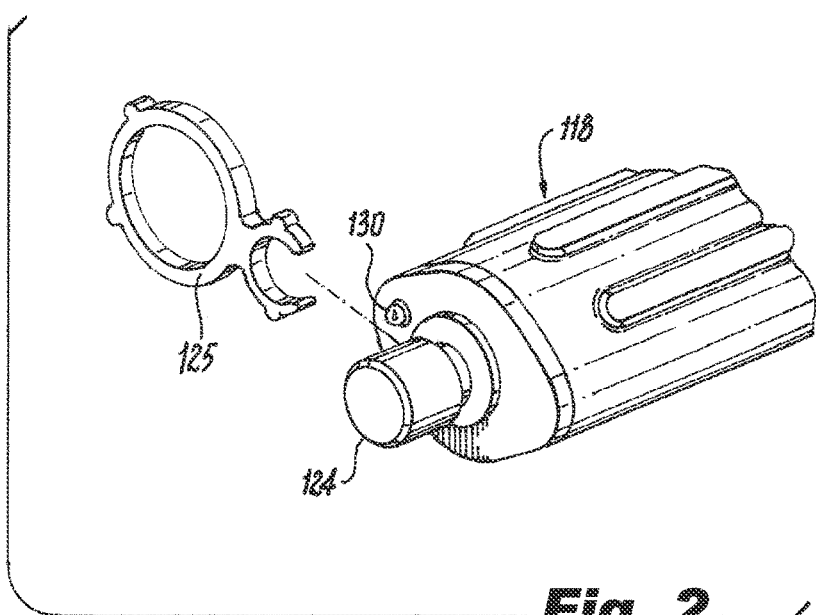
FIG. 2 is a localized perspective view of the proximal end of the handle portion of the catheter device of FIG. 1.

As best seen in FIGS. 2 and 4, a push-button switch 124 is provided on the proximal end of the handle assembly 118 for manually actuating the catheter device 110 to control the LED light source(s) by way of the controller 128. An LED indicator light 130 is provided on the exterior of the handle assembly 118 adjacent the switch 124 to provide a visual indication that the catheter device 110 is activated. It is envisioned that an audible signal generator may also be provided to indicate that the catheter device 110 is in use.

A locking clasp 125 is provided for immobilizing the switch 124 to prevent the catheter device 110 from being inadvertently turned on or off. The clasp 125 can be removed by a user t actuate the switch 124. It is further envisioned that the catheter device 110 may be provided with a timing circuit for controlling the duration of ultraviolet light therapy, and a visual or audible alarm may be associated with the timing circuit to provide an indication to a user that the time period has ended.

Figure 5:
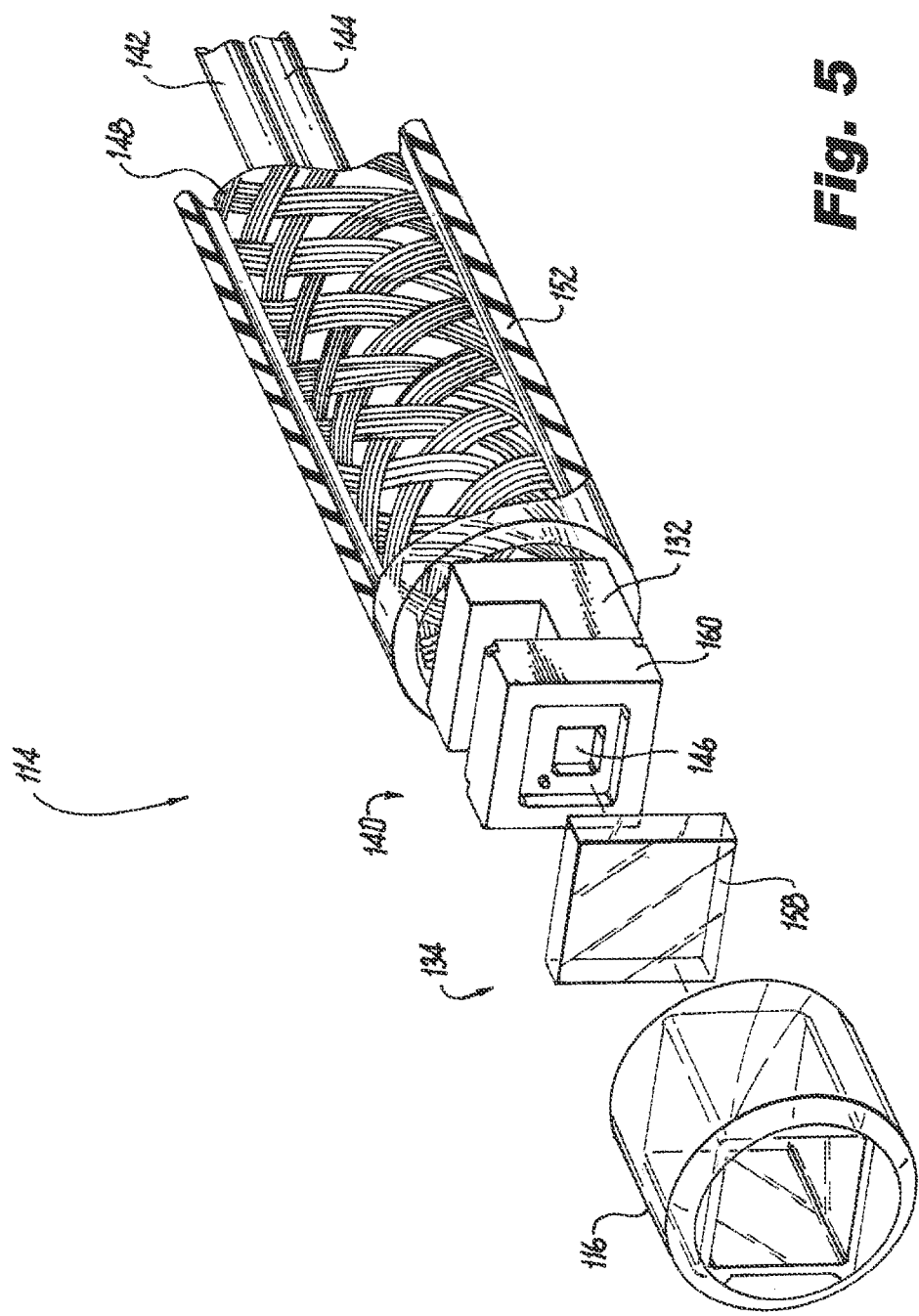
FIG. 5 is an exploded perspective view of the distal end portion of the catheter device of FIG. 1, with parts separated for ease of illustration.

Referring now to FIG. 5, catheter device 110 further includes an illumination assembly 134 that is operatively associated with a distal end portion of the catheter body 112. The illumination assembly 134 is encased within the cylindrical tip section 116 at the distal end portion 114 of the catheter body 112. The illumination assembly 134 includes a microchip assembly 140 containing an LED light source 146 that is supported within a housing 160, which is positioned to face distally. A quartz glass window 158 is positioned distal to the housing 160 in front of the LED light source 146. The illumination assembly 134 further includes a metallic coupler 132 which is located behind the housing 160 of the microchip assembly 140 and which couples or otherwise operatively connects the illumination assembly 134 to the distal end of catheter body 112. Preferably, the coupler 132 is formed from brass or a similar metallic material that readily conducts heat.

It is envisioned that the LED light source 146 would produce a radiance pattern of about 120 degrees with an effectivity distance of about 3.0 cm. The LED light source 146 is adapted and configured to generate UVC radiation at a wavelength of about between 240-350 nm, preferably at a wavelength of 265 nm. Treatment for 60-70 seconds at an irradiance of 17 mW/cm$^2$, results in a dose of about 1 J/cm$^2$ measured at a wavelength of 265 nm. The LED light source 146 is configured so that light intensity output remains constant during use, with 1% or less variation over 8 hours of continuous use.

Figure 6:
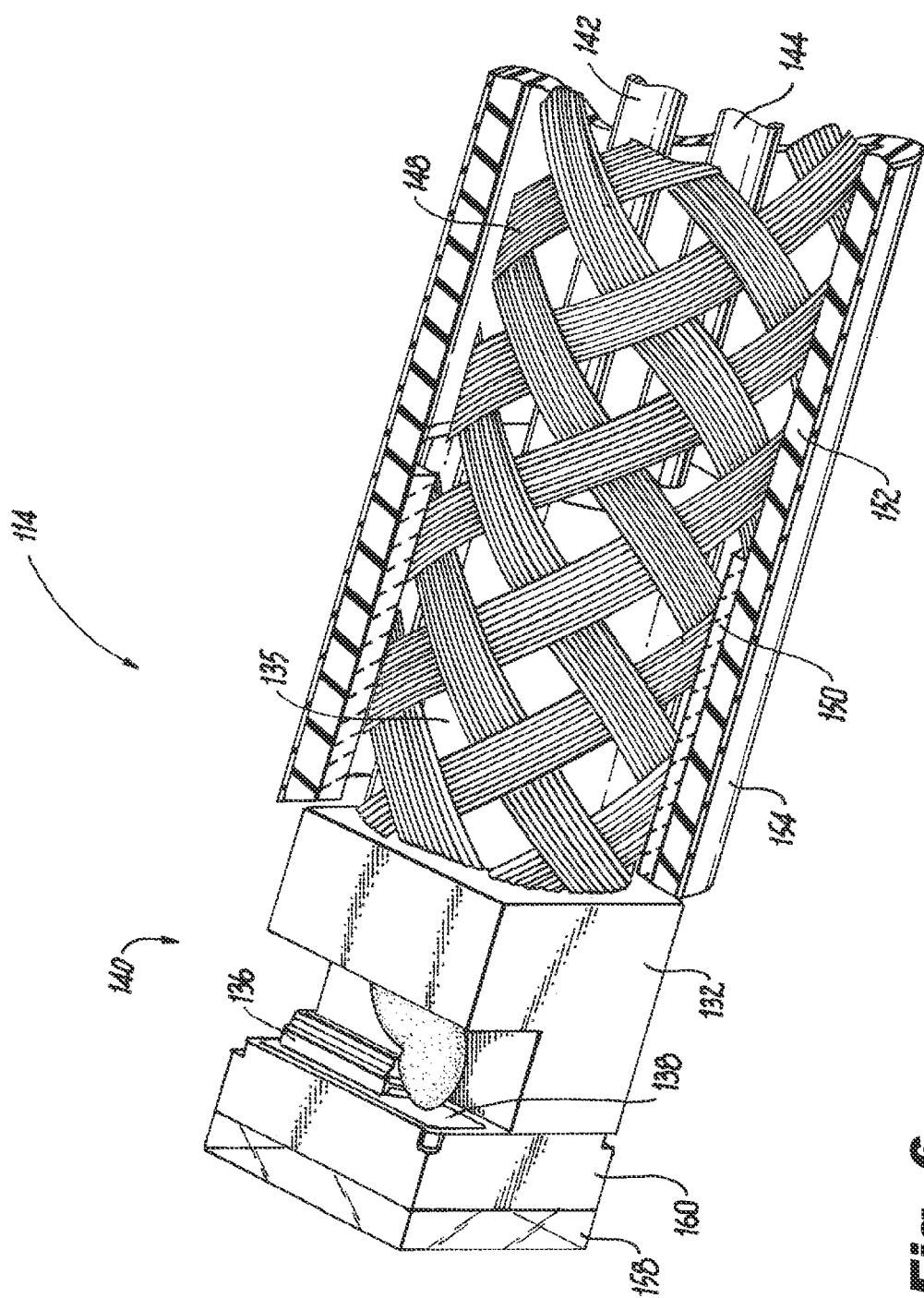
FIG. 6 is an enlarged perspective view of the distal end portion of the catheter body, illustrating the coupler and elongated braided sleeve, forming a heat sink for the device.
Figure 15:
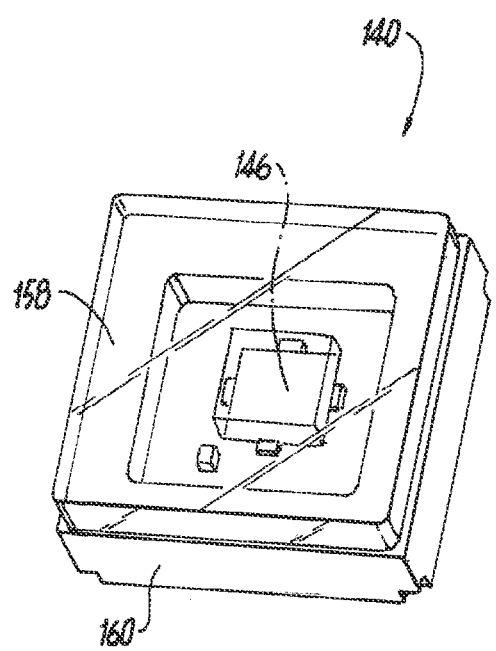
FIGS. 15 and 16 are enlarged perspective views of the housing and quartz glass within the microchip assembly which forms part of the illumination assembly shown in FIG. 13.
Figure 16:
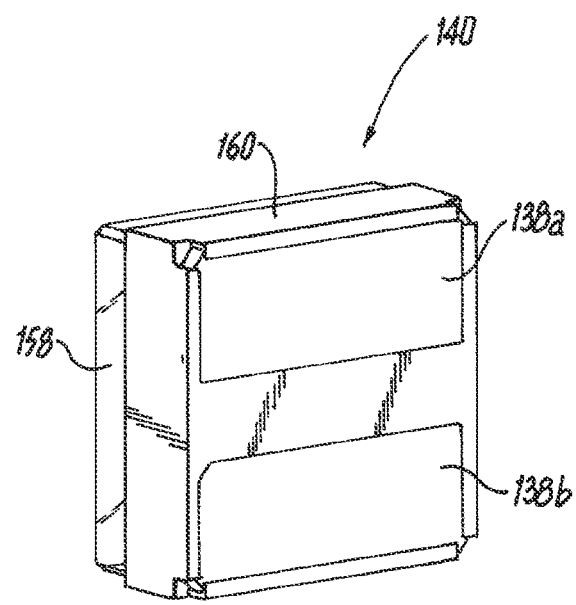
Figure 17:
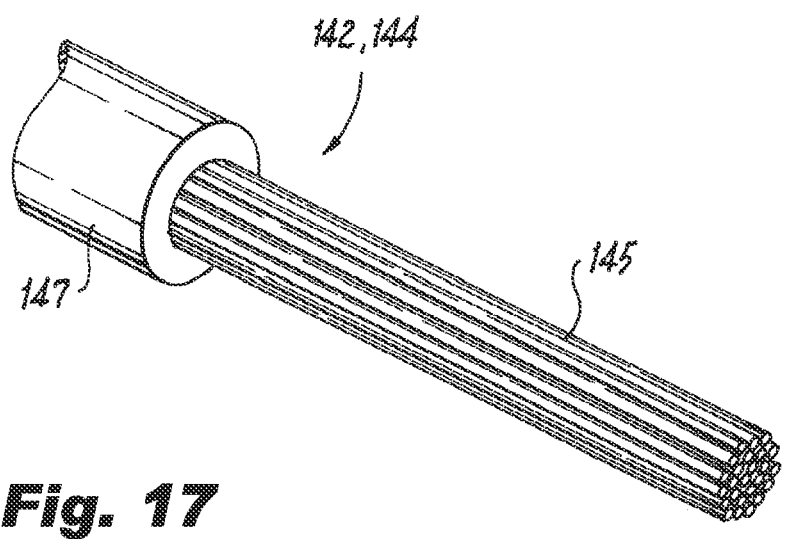
FIG. 17 is an enlarged perspective view of one of the conductors shown in FIG. 14.

Referring to FIG. 6, the housing 160 includes back contact plates 138a, 138b formed from gold or a similar precious metal for connecting the LED light source 146 within the housing 160 to a cathode conductor 142 and an anode conductor 144 (see also FIGS. 15 and 16). A solder joint 136 is used to join the contact plates 138a, 138b to the conductors 142, 144, respectively. Preferably, the solder used for joining is a silver based solder material and the conductors 142, 144 are made from tinned copper wires 145 surrounded by an insulating sheath 147, as best seen in FIG. 17. The tinned copper conductors 142 and 144 extend distally from the handle assembly 118 to the illumination assembly 134 via the brass coupler 132 in order to deliver power from the one or more batteries 164a-164f.

With continuing reference to FIG. 6, the elongated catheter body 112 includes a relatively soft thermoplastic shaft 152 formed from a materials such as Pellethane® or the like that is surrounded by a relatively thin thermoplastic sheath 154 formed from a material such as polyurethane or the like. An elongated braided sleeve 148 extends along a length of the inner shaft 152 and it is operatively associated with the proximal extension portion 135 of the brass coupler 132. A cylindrical compression sleeve 150 at the distal end of shaft 152 surrounds and securely compresses a distal end portion the elongated braided sleeve 148 around the proximal extension portion 135 of the brass coupler 132 so that it is well managed.

The braided sleeve 148 is fabricated from a plurality of tinned copper wires and it is adapted to serve as a thermal sink for heat generated by the illumination assembly 134. More particularly, the brass coupler 132, 135 transfers heat from the LED light source of the illumination assembly 134 to the elongated braided sleeve 148. In addition, the thermoplastic outer sheath 154 surrounding the catheter body 112 can reduce surface heat generated by the illumination assembly 134. It is envisioned that surface heat can also be reduced at the tip section 116 via a ceramic or polycarbonate tip cover.

Figure 7:
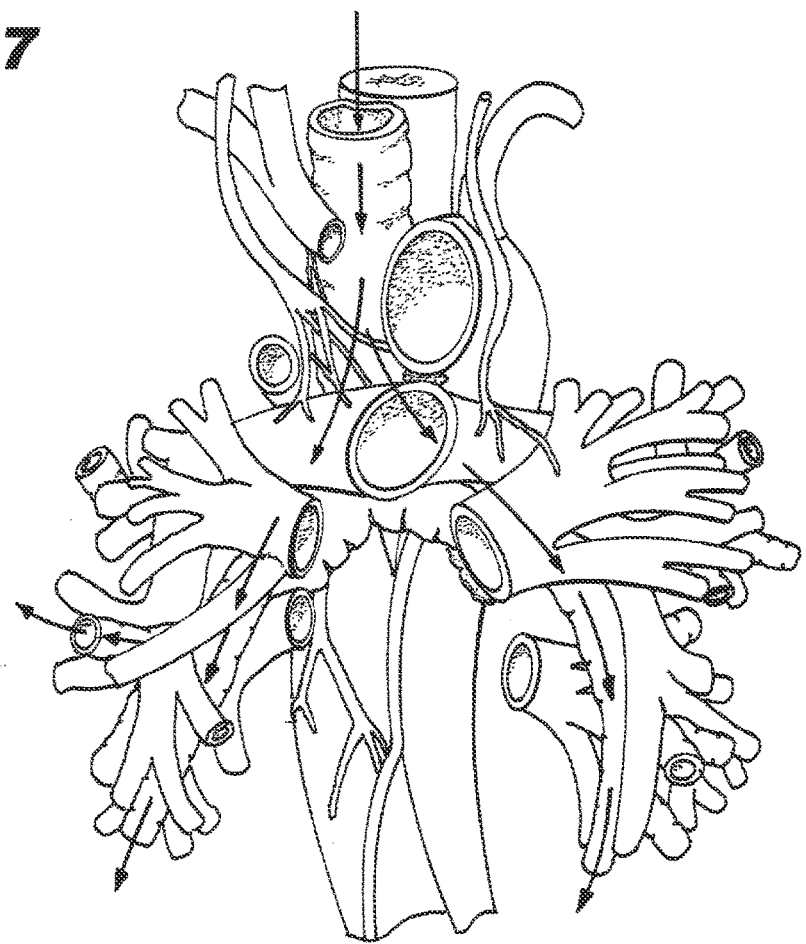
FIG. 7 is an illustration of the areas of the pulmonary system in which the catheter system of the subject invention can be introduced to perform endobronchial ultraviolet therapy with one LED light source.
Figure 8:
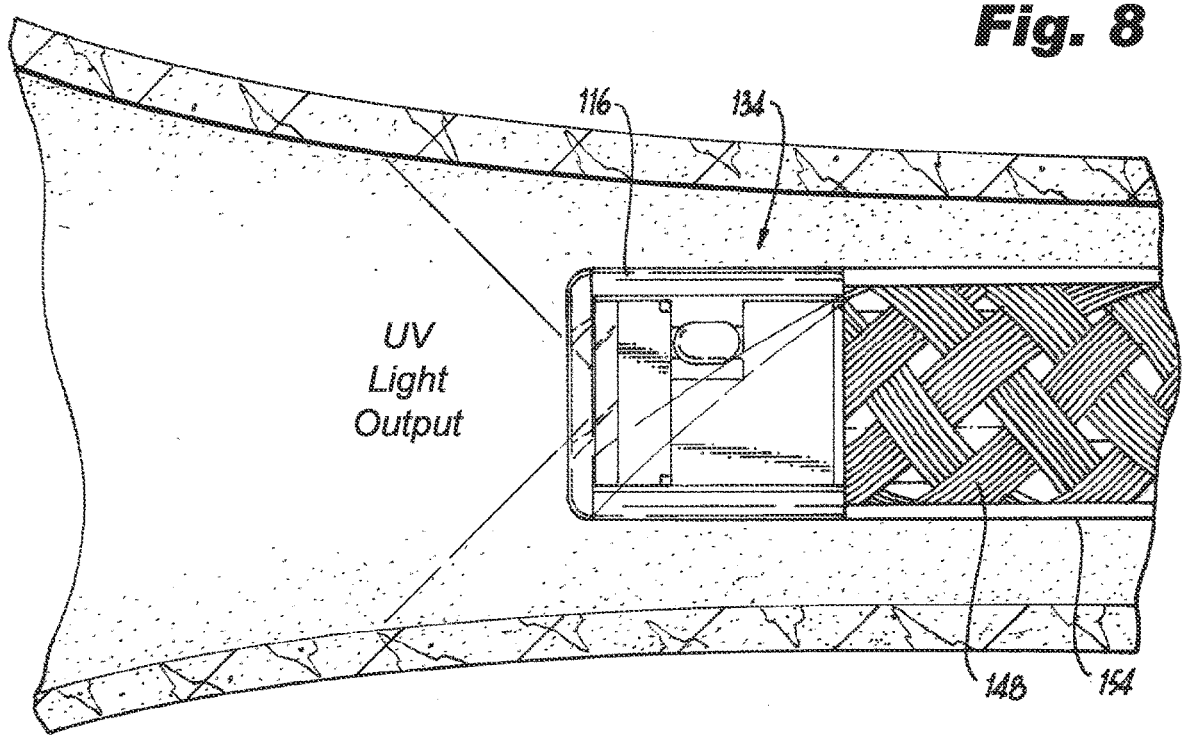
FIG. 8 shows the distal end portion of the catheter device of FIG. 1 positioned within a bronchial passage.

Referring to FIG. 7, there is illustrated the preferred path(s) of introduction of the catheter device 110 into areas of the pulmonary system to perform endobronchial ultraviolet therapy with the illumination assembly 134. More particularly, as shown in FIG. 8, when the distal tip section 116 of the catheter device 110 is positioned at a desired location within a bronchial passage, the illumination assembly 134 may be activated for ultraviolet light therapy in the pulmonary system of the patient to reduce viral, fungal and/or bacterial loads.

Referring now to FIG. 9, there is illustrated another catheter device constructed in accordance with a preferred embodiment of the subject invention and designated generally by reference numeral 210. As explained in more detail below, catheter device 210 is similar in many respect to the catheter device 110 described above, in that it includes an elongated flexible catheter body 212, a handle assembly 218 and an illumination assembly 234 operatively associated with a distal end portion 214 of the catheter body 212. And, as in the previous embodiment of the subject invention, the handle assembly 218 houses a controller 228 for managing the functions of the illumination assembly 234 and a power source 264 for powering the illumination assembly 234. The handle assembly 218 also includes an actuation switch 224 and an indicator light 230.

The catheter device 210 differs from the previously described embodiment of the subject invention in that the illumination assembly 234 associated with the distal end portion of the catheter body 212 is multi-faceted in that it includes three separate LED light sources, each facing in a different direction, to provide a relatively enlarged treatment area for the application of UVC radiation at a wavelength of about between 240-350 nm, preferably at a wavelength of 265 nm.

Figure 12:
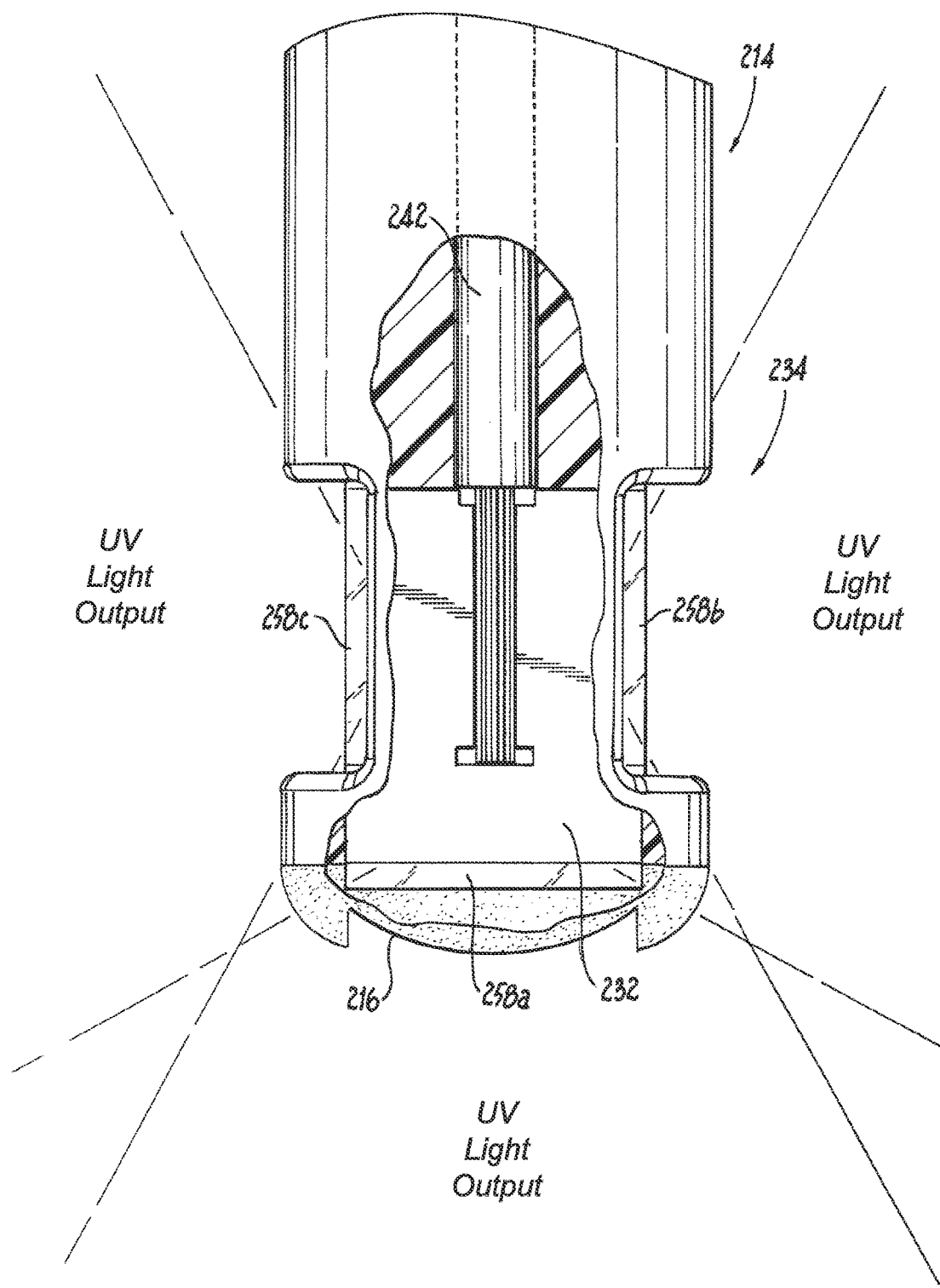
FIG. 12 is an enlarged elevational view of the distal end portion of the catheter device of FIG. 9, partially broken away to illustrate the internal components, and showing the illumination pattern of the three LED light sources therein.
Figure 18:
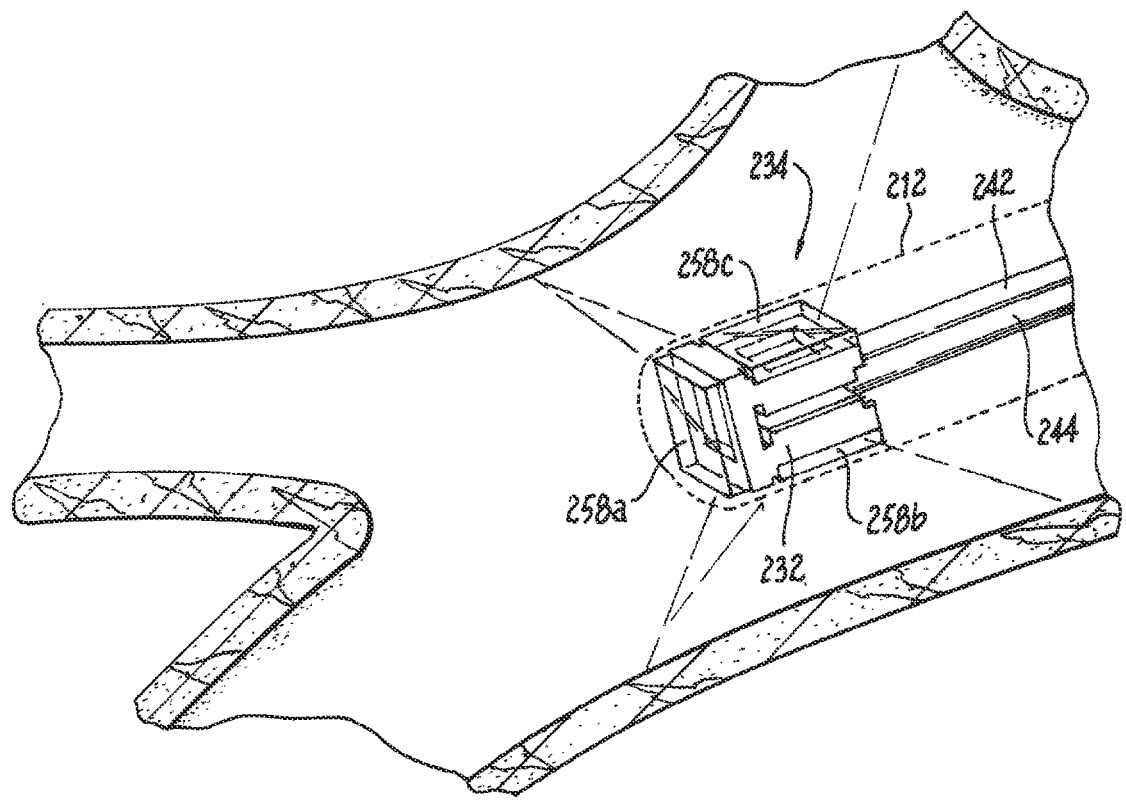
FIG. 18 is an illustration of the catheter device of FIG. 9 within the bronchial system of a patient to perform endobronchial ultraviolet therapy with three LED light sources.

More particularly, as shown in FIGS. 10 through 12, the illumination assembly 234 includes at least three (3) LED microchip assemblies 140. These three assemblies include a first LED light source 246a supported in a housing 260a facing distally through a quartz glass lens 258a, a second LED light source 246b supported in a housing 260b facing to the right through a right side quartz glass lens 258b, and a third LED light source 246c supported in a housing 260c and facing to the left through a left side quartz glass lens 258c. Together, the three microchip based LED light sources produce a 3-dimensional radiance pattern that is illustrated by way of example in FIGS. 12 and 18. Preferably, the illumination assembly 234 provides a radiance pattern that covers an area of about 120 degrees with an effectivity distance of about 3.0 cm or more.

Figure 13:
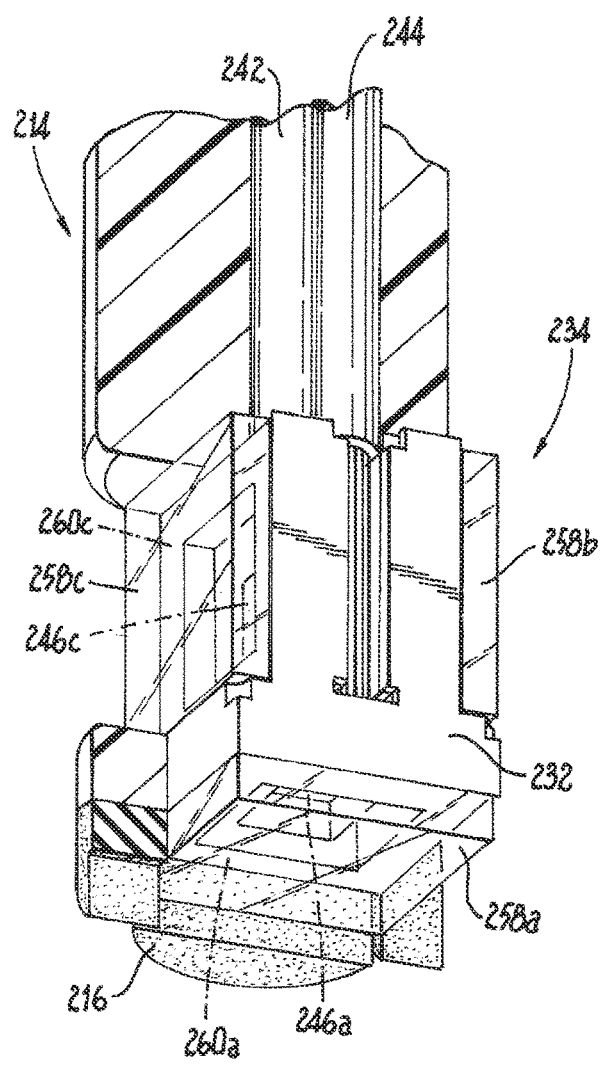
FIG. 13 is an enlarged cross-sectional perspective view of the illumination assembly of the catheter device shown in FIG. 9.
Figure 14:
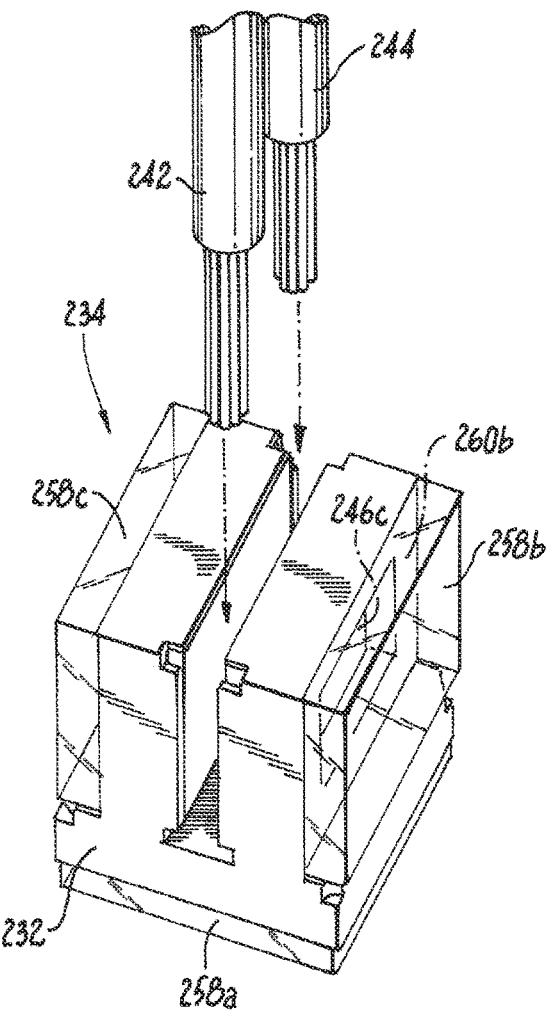
FIG. 14 is an exploded enlarged perspective view of the conductors separated from the illumination assembly shown in FIG. 13.

The three housing 260a, 260b and 260c are all operatively supported within a coupler 232 (e.g., a brass coupler) located within the distal end portion 214 of the catheter body 212, which has an atraumatic tip 216. The coupler 232 is electrically connected to the anode and cathode conductors 262 and 264, as best seen in FIGS. 13 and 14. These conductors 242, 244 and associated heat sinks (e.g., a braided sleeve(s) made of tinned copper wires), extend through the catheter body 112, 212 from the proximal handle portion 118, 218 to the LED based microchip assemblies to connect with a cathode and anode conductors of each assembly to provide power thereto.

Referring to FIGS. 15 and 16, there is illustrated an exemplary LED microchip assembly 140 of the subject invention, which includes an LED light source 146 for producing UV light radiance or illuminance that is encapsulated in square housing 160 having a quartz glass lens 158. Anode and cathode back plates 138a, 138b, formed from a precious metal, provide connection points for the anode and cathode conductors 242, 244, respectively, as explained previously. The dimensions of each housing 160 is about 3.50 mm×3.50 mm, so that three assemblies 140 can be easily mounted within the distal end portion of a catheter body 212. Exemplary microchip based LED light sources are manufactured by Sensor Electronic Technology, Inc. of Columbia, S.C.

Figure 19:
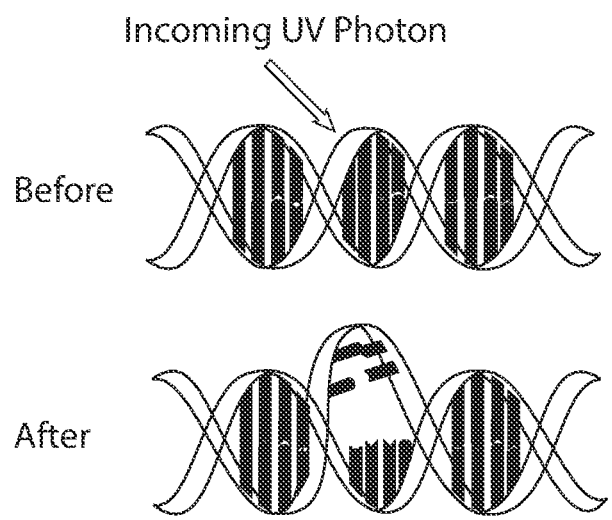
FIG. 19 is an illustration showing the disinfecting effect of UV radiation on microbial DNA strands.
Figure 20:
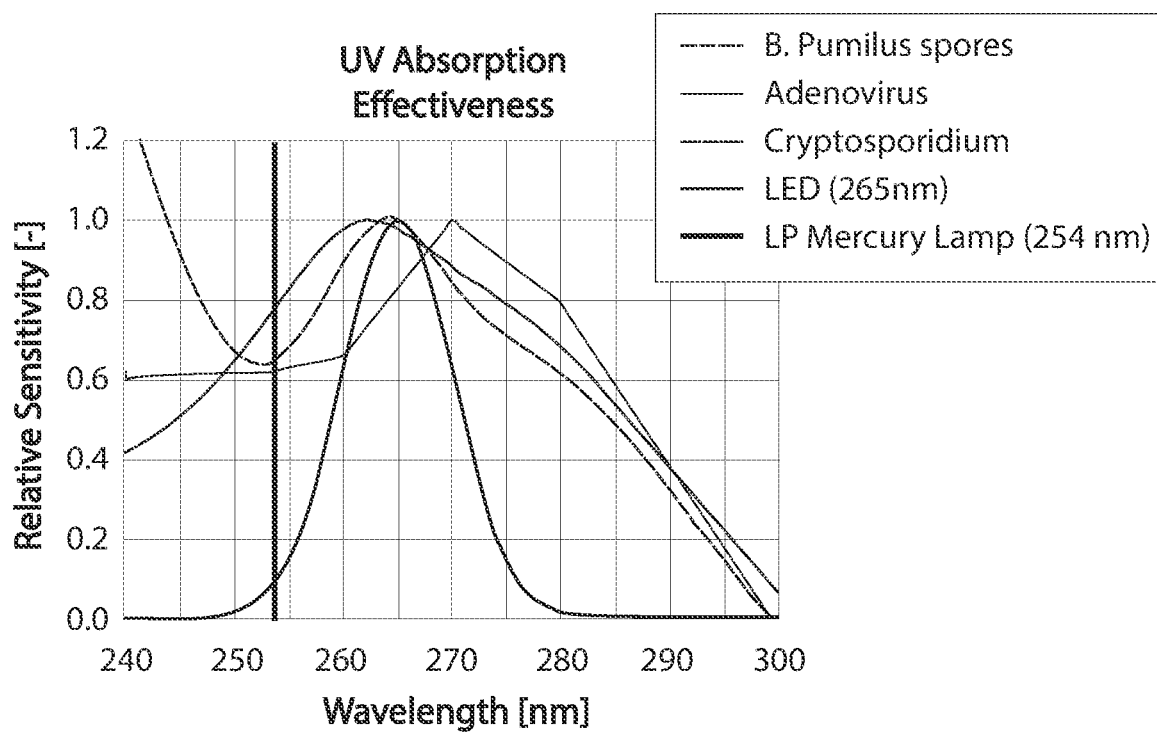
FIG. 20 is an illustration showing UV absorption effectiveness as applied to various microbes.

The catheter devices 110, 210 of the subject invention are intended for use in the treatment of pulmonary diseases via direct germicidal radiation of light at a UVC wavelength in the range of 240-350 nm, and preferably, at a wavelength of about 265 nm inside the bronchial system and lungs, disrupting the reproductive ability of invading microorganisms. This not only reduces the viral load in the respiratory apparatus but also in the oxygenated and deoxygenated blood along the bronchial system, thereby reducing overall viral load in the patient's body. Support for these contentions is shown in FIGS. 19-20, illustrating the disinfection effect of UV light on microbial DNA strands, and UV absorption effectiveness as applied to various microbes.

The subject invention is also directed to a method of reducing viral and bacterial loads in a patient's pulmonary system by way of endobronchial ultraviolet light therapy. The method includes the step of introducing a source of UV light radiance into the pulmonary system of a patient. More particularly, the method includes introducing a pulmonary catheter 110, 210 constructed in accordance with the subject invention through a side port of a three way valve of a ventilator system, so that patient ventilation continues without interruption. Alternatively, the catheter 112, 210 can be administered directly through an endotracheal tube assembly after a routine protocol, such as hyperventilating the lungs for suction therapy. Alternatively, the catheter 110, 210 of the subject invention may be administered through the side port of a bronchoscope.

It is envisioned that the pulmonary catheter of the subject invention can be used for treating: the nasal cavity/nostril (right and left); the nasopharynx, oropharynx and laryngopharynx; the larynx and trachea; and treatment of the left bronchus and lobar bronchus.

Through manipulation by the user administering the therapy under vision, the catheter device 110, 210 can be easily passed to either the right or left main bronchus. Once the device is positioned at a selected site within the bronchial segment of the lung, the site is illuminated with UV light at a wavelength in the range of 240-350 nm, and preferably a wavelength of about 265 nm, for a predetermined period of time. This ultraviolet light therapy is intended to effectively disrupt microbial activity at the site and its vicinity. The device can be manually rotated by the user to provide the ultraviolet light therapy circumferentially and axially with respect to the selected site.

While the subject disclosure has been shown and described with reference to preferred embodiments, those skilled in the art will readily appreciate that changes or modifications may be made thereto without departing from the spirit or scope of the subject disclosure.

What is claimed is:

1. A catheter for performing ultraviolet light therapy in a pulmonary system of a patient, comprising:
    a) an elongated flexible catheter body defining a longitudinal axis and having opposed proximal and distal end portions;
    b) a handle assembly operatively associated with the proximal end portion of the catheter body;
    c) an illumination assembly operatively associated with the distal end portion of the catheter body and configured to emit ultraviolet light radiance to reduce viral, fungal and/or bacterial loads in the pulmonary system of the patient, wherein the illumination assembly includes a first LED light source facing in a first direction, a second LED light source facing in a second direction, and a third LED light source facing in a third direction, and wherein a first quartz glass window disposed in a first plane extending perpendicular to the longitudinal axis of the catheter body is distally adjacent to the first LED light source, a second quartz glass window disposed in a second plane extending parallel to the longitudinal axis of the catheter body is laterally adjacent to the second LED light source, and a third quartz glass window disposed in a third plane extending parallel to the longitudinal axis of the catheter body is laterally adjacent to the third LED light source; and
    d) an elongated braided sleeve disposed within the catheter body and extending along a length thereof for serving as a heat sink for the illumination assembly.

2. A catheter as recited in claim 1, wherein the illumination assembly includes a coupler connected to a distal end portion of the catheter body.

3. A catheter as recited in claim 2, wherein each LED light source is operatively connected to the coupler.

4. A catheter as recited in claim 3, wherein the coupler is configured to transfer heat from the illumination assembly to the braided sleeve.

5. A catheter as recited in claim 1, wherein the braided sleeve is enclosed by a compression ring at the distal end portion of the catheter body.

6. A catheter as recited in claim 1, wherein the braided sleeve is formed from tinned copper wires.

7. A catheter as recited in claim 1, wherein the illumination assembly is enclosed within a polycarbonate tip cover which extends proximally therefrom for reducing surface heat.

8. A catheter as recited in claim 1, wherein the illumination assembly is enclosed within a ceramic tip cover which extends proximally therefrom for reducing surface heat.

9. A catheter as recited in claim 3, wherein each LED light source is configured to generate UVC radiation at a wavelength of about 240-350 nm.

10. A catheter as recited in claim 9, wherein each LED light source is configured to generate UVC radiation at a wavelength of about 265 nm.

11. A catheter as recited in claim 1, wherein the first LED light source faces in a distal direction, the second LED light source faces in a first lateral direction orthogonal to the first LED light source, and the third LED light source faces in a second lateral direction that is opposite from the first lateral direction relative to the longitudinal axis of the catheter body.

12. A catheter as recited in claim 3, wherein each LED light source is supported on a microchip, and wherein each microchip is disposed within a housing.

13. A catheter system as recited in claim 1, wherein the handle assembly is configured to receive a power source for delivering power to the illumination assembly through the elongated catheter body.

14. A catheter as recited in claim 13, wherein the handle assembly includes a switch for manually activating the power source.

15. A catheter as recited in claim 14, wherein the handle assembly includes a locking pin for immobilizing the switch.

16. A catheter as recited in claim 14, wherein the handle assembly includes an indicator for communicating to a user that the power source is activated.

17. A catheter as recited in claim 1, wherein the catheter body includes a coating of thermoplastic polyurethane and has an operative length of about 40.0 to 50.0 cm and an outer diameter of about 5.5 mm.

18. A catheter as recited in claim 13, wherein conductors extend from the handle assembly to the illumination assembly to deliver power from the power source, and the conductors are formed of tinned copper wires.

* * * * *